United States Patent
Slettenmark

[11] Patent Number: 5,707,361
[45] Date of Patent: Jan. 13, 1998

[54] IMPLANTABLE INFUSION SYSTEM WITH A NEUTRAL PRESSURE MEDICATION CONTAINER

[75] Inventor: Bruno Slettenmark, Jaefaella, Sweden

[73] Assignee: Siemens Aktiengesellscahaft, Munich, Germany

[21] Appl. No.: 400,954

[22] Filed: Mar. 8, 1995

[30] Foreign Application Priority Data

Mar. 10, 1994 [SE] Sweden .................. 9400821

[51] Int. Cl.⁶ .................. A61M 37/00; A61M 11/00
[52] U.S. Cl. .................. 604/131; 604/93; 604/133; 604/151; 604/153
[58] Field of Search .................. 604/131, 132, 604/133, 134, 140, 141, 142, 143, 145, 151, 152, 153, 93

[56] References Cited

U.S. PATENT DOCUMENTS

| | | |
|---|---|---|
| 4,191,181 | 3/1980 | Franetzki et al. |
| 4,511,355 | 4/1985 | Franetzki et al. |
| 4,772,263 | 9/1988 | Dorman et al. .................. 604/132 |
| 5,006,115 | 4/1991 | McDonald .................. 604/93 X |
| 5,176,644 | 1/1993 | Srisathapat et al. .................. 604/141 |
| 5,514,103 | 5/1996 | Srisathapat et al. .................. 604/141 |

FOREIGN PATENT DOCUMENTS

| | | |
|---|---|---|
| 0 387 439 | 9/1990 | European Pat. Off. |
| 2 131 496 | 6/1984 | United Kingdom. |

*Primary Examiner*—Sam Rimell
*Assistant Examiner*—Robert V. Racunas
*Attorney, Agent, or Firm*—Hill, Steadman & Simpson

[57] ABSTRACT

An implantable infusion system has a neutral pressure medication supply container for liquid medication to be delivered to the patient, the supply container being devised so that its volume changes according to the amount of medication it contains, and a pump for pumping medication from the supply container, via a catheter, to the patient's body. The supply container and the pump are arranged inside an enclosure to which the catheter is connectable at the output of the pump. A closed space, at least partly contained inside the enclosure, in which the supply container is arranged, and in which essentially atmospheric pressure prevails, is arranged to change its volume to a corresponding degree when the volume of the supply container changes, so that the pressure is kept essentially unchanged.

35 Claims, 4 Drawing Sheets

IMPLANTABLE INFUSION SYSTEM WITH A NEUTRAL PRESSURE MEDICATION CONTAINER

BACKGROUND OF THE INVENTION

1. Field of the Invention

The present invention relates to an implantable infusion system, of the type having a neutral pressure medication supply container for liquid medication to be delivered to the patient, the supply container being devised so that its volume changes according to the amount of medication it contains, and a pump for pumping medication from the supply container, via a catheter, to the patient's body, the supply container and the pump being arranged inside an enclosure to which the catheter is connectable at the output of the pump.

2. Description of the Prior Art

In implantable systems of the above general type, the outlet valve is a key component for patient safety and dispensing accuracy. During the estimated service life of the infusion system, assuring compliance with the exceptionally stringent demands made on sealing ability of the valve is very difficult.

One known solution for preventing delivery of excessive doses of medication to the patient if a fault appears in the system is to maintain a negative pressure of e.g. about 700 mbars absolute, in relation to the surroundings, in the insulin container, see e.g. U.S. Pat. No. 4,191,181. A leaking outlet valve in such a system causes a flow into the container because of the lower pressure therein, but no medication flows out into the patient's body.

In implanted infusion systems, the use of higher concentrations of the active substance in the drug to be administered is desirable so that the size of the implant can be reduced and/or the interval between refills prolonged. This makes even greater demands on the sealing ability of the valve, since the emitted flow is correspondingly smaller.

Thus, a constant pressure difference of, typically, 300 mbars across the outlet valve prevails in the above described known infusion system. Even a very slight valve leakage, e.g. on the order of a fraction of a Kl/hour, thus induces a continuous retrograde flow through the valve. The pump operates intermittently with, typically, µl/6 min. at this flow and with 1 µl/10 sec. at a bolus flow, and a minimum flow can amount to 1 µl/10 to 30 minutes. Valve leakage causes a major or minor relative fault in these programmed flows, depending on the magnitude of programmed flow and the magnitude of valve leakage. The relative effect of a given valve leakage increases when the concentration of medication in the fluid increases. Thus valve leakage causes varying deviations in the intended flow which can be considerable and can affect the therapy.

When there is valve leakage, body fluid and/or blood are thus sucked inwardly through the catheter tip when the pump is inactive between each pulse discharge because of the negative pressure in the medication container. Depending on the magnitude of the leakage and the time elapsing between each pulse discharge, the distance that the body fluid penetrates into the catheter varies. For a catheter used in practice, this distance could, typically, amount to 15 mm/µl very likely this will lead to catheter blockage after a time because of the aggregation of proteins, formation of fibrin, etc. Catheter blockage is currently the biggest problem in implantable infusion systems. Further the infusion system probably must be replaced if body fluid penetrates all the way into the pump and medication container.

In addition, the safety system, which is based on a negative pressure in the medication container, could be made inoperative in certain situations. When the medication container is, e.g., overfilled with fluid or air, causing it to bottom out inside the enclosure, a pressure of about 1 bar develops in the container. In the case of active overfilling caused by incorrect handling, a much higher pressure can develop in the container. When valve leakage is considerable or a valve becomes inoperative, body fluid can be sucked into the medication container and the container bottoms out, with pressure in the container then amounting to about 1 bar. In the event of leakage in the outer enclosure directly into the medication container, body fluid is sucked inwardly until the container bottoms out, and the pressure reaches about 1 bar. If, in addition, the container, which is often devised as a bellows container, sticks in an intermediate position, the container pressure can amount, in certain circumstances, to about 1 bar.

If the ambient pressure then drops, which could happen during an air flight, on a trip to a high altitude location, etc., while the refill septum or outlet valve is leaking, unchecked amounts of infusion fluid could leak into the patient with very harmful effects as a result. In these instances, the occurrence of only relatively slight mechanical pressure on the implanted system could cause medication leakage. At altitudes above 3,000 m, the pressure in the container further exceeds the ambient pressure and then leakage from the container would always be a risk. The container pressure also rises when the temperature of the implanted system is higher than intended (37 degrees Celsius), causing an attendant safety hazard. The volume pumped is also affected by both the temperature of the implant and the ambient pressure. The differential pressure across the container's outlet valve governs the degree to which the valve opens, and the freon pressure is temperature-dependent.

Another disadvantage of the known "negative pressure system" is the fact that the pressure difference between the container and the surroundings, i.e. typically 300 mbars, must be overcome by the pump at each pump stroke. A pressure of 300 mbars corresponds to a force of about 0.1N on the valve. This accounts for about 15% of the pump's energy consumption. Pump pressure must also be high enough to overcome the sealing force of the valve and lift the valve during the expulsion phase. In contemporary systems, the sealing force corresponds to a pressure difference of about 1 bar. The energy consumption for the valve opening corresponds to about 50–60% of the energy consumption of the valve.

New pumping principles, such as pumps devised with silicon/micromechanics and employing piezoelectric or thermal activation, electro-osmotic pumps, EHD pumps, etc., which are capable of supplying stipulated fluid flows, are of interest in the future development of implantable infusion systems. A characteristic shared by many of these pumps is that they are only able to achieve a very low static pressure, typically from 1 mbar up to a few tens of mbars. Thus they cannot be used in the above-described negative pressure systems.

Another problem with known negative pressure systems is due to the circumstance that the pressure in the pump chamber drops sharply and chamber fluid starts *cavitating if the piston's retraction force, at the end of a piston stroke, exceeds a given value when the pump chamber is refilled. Cavitation develops in the pump chamber when the retraction force exceeds about 0.2N at a pressure of 700 mbars in the container and when the retraction force exceeds 0.3N at 1,000 mbars with the pumps used. Cavitation in medication fluid should be avoided when the fluid contains delicate molecules which could then be damaged, e.g. be denatured, aggregated, acquire changed biological properties, become adhered to surfaces in the fluid path, thereby affecting the valve function or causing a blockage in the catheter. Insulin is a substance made of such sensitive molecules. In order to minimize the risk of piston "hangup" caused by the capillary force in the airfluid interface, if air should cross the gap between the piston and the container wall moreover there is a requirement that the pumps in question must be capable of pumping air-water mixtures) or for other reasons, such as friction or adherence to the valve surface, the pumps in question must develop a retraction force of about 0.25N, which is the highest value during a retraction operation with increasing force. Thus fluid in the pump chamber cavitates during the latter part of the pump's return. In a similar manner, fluid pressure drops behind the piston, i.e on the pump's inlet side, because of mass forces in the fluid and flow resistance in the inlet tube at the actual pump stroke.

The negative pressure in the medication container also subjects the septum, through which the container is refilled with medication at regular intervals, to a negative pressure of about 300 mbars. Small amounts of body fluid leak through the septum into the container when the injection cannula is introduced and/or withdrawn when medication is refilled. During the filling operation, which first involves evacuation of the container to a pressure of about 60 mbars, followed by sucking in fluid, there is risk that air could simultaneously be sucked into the container if any part of the filling equipment, such as taps, couplings etc., were to start leaking. The presence of air in the medication container is often extremely unsuitable, even hazardous, especially in systems intended for the infusion of insulin. Ascertaining when there is less than 3 ml of air in the medication container after filling is currently not possible. In the course of time, moreover, the number of cannula punctures made in the refill septum will become considerable, typically a hundred or more, and an absolutely leak-proof septum cannot be guaranteed, especially if a number of cannula punctures are adjacent to each other. Because of the pressure difference, leakage of body fluid or free gas in the implant pocket into the container is always a risk during the 4 to 6 weeks which elapse between refills. Even small amounts of body fluid in the medication container can affect the medication, produce precipitations, block filters, have an adverse effect on pump and valve function and contribute to catheter blockage.

There are also types of valve constructions in which the sealing washer is not attached to the valve's metal part, so fluid on the pump's outlet side could be sucked in behind the sealing washer because of the pressure difference between the outlet sides of the pump chamber and of the pump. The sealing washer will then bulge into the pump chamber, causing a drop in the volume pumped in each pump stroke, sometimes by as much as 25–35%, or a certain amount of body fluid could be sucked into the catheter after every pump stroke, typically a distance of 3–4 mm into the catheter. This accelerates blockage of the catheter tip.

The above-described problems can be solved to some degree by "positive pressure systems", i.e. infusion systems with a positive pressure in the medication container in relation to ambient pressure, the positive pressure serving as a driving force for pumping out medication, see e.g. European Patent 0,387,439. A disadvantage of such positive pressure systems, however, is that leakage of disastrously large amounts of medication into the patient in the event of valve leakage, enclosure leakage, septum leakage, when medication containers are refilled etc. is a major risk with these systems.

So-called "neutral pressure systems" eliminate the above discussed problems of "negative pressure systems" and are not associated with any of the risks of "positive pressure systems". Such neutral pressure systems are known from British Specification 2,131,496 and U.S. Pat. No. 4,511,355. Such neutral pressure systems ensure that the pressure in the medication container is essentially the same as the pressure at the catheter tip and the atmospheric pressure, irrespective of the atmospheric pressure and the temperature of the implant. In British Specification 2,131,498 an implantable infusion system is disclosed which has openings in the enclosure so that the space inside it, but outside the medication container, is in communication with the implant's surroundings in the patient. The pressure in this space inside the enclosure, which accordingly acts on the medication container, is therefore the same as pressure outside the implant. The structure shown in this publication, however, cannot be used for, e.g., infusing insulin. If the container were to break, the consequences to the patient would be devastating. An implantable infusion system is described in U.S. Pat. No. 4,511,355 in which a part of the enclosure consists of a membrane made from a hydrophobic material, permeable to gas, which ensures that essentially the same pressure prevails inside the enclosure as outside it. Body fluids, as well as cells and bacteria, are, however, prevented from passing the membrane. The disadvantage of this design is that a simple sealing defect could be very harmful to the patient.

SUMMARY OF THE INVENTION

An object of the present invention is to provide a new, implantable, neutral pressure infusion system with greatly improved patient safety and in which body fluid is unable to penetrate into the enclosure of the implant.

The above object is achieved in accordance with the principles of the present invention in an implantable infusion system having a neutral pressure medication supply container for liquid medication to be delivered to a patient, the supply container being devised so that its volume changes according to the amount of medication contained therein, and a pump for pumping medication from the supply container, via a catheter, to the patient's body. The supply container and the pump are contained inside an enclosure, to which the catheter is connectable at the output of the pump. The system includes a closed space, at least partially contained within the enclosure, in which the supply container is disposed and in which pressure which is essentially equal to atmospheric pressure prevails. The closed space is devised so as to be capable of changing its volume to a corresponding degree when the volume of the supply container changes, so that the pressure is maintained substantially unchanged.

With the system according to the invention, valve leakage is eliminated if the valve should not be leakproof, and delivery of the intended flow is assured. The most likely main cause of catheter blockage, viz. suction and aggregation of proteins etc., is also eliminated. The system according to the invention is completely insensitive to ambient pressure and implant temperature, as well as to the presence of air in the medication container. The critical importance of the valve as a component is greatly reduced, the risk of valve leakage is eliminated and the pumped chamber volume becomes independent of ambient pressure and implant temperature, with increased patient safety as a result. The energy consumption of the infusion system is also reduced, thereby increasing the life of the implant or alternatively of the energy source, which makes a reduction of the volume and weight of the battery possible and, accordingly, the volume and weight of the implant. With the infusion system according to the invention, the energy consumption of the pump and, thus, of the implant, is reduced by about 30% which increases the life of the implant by about 30% or, alternatively, reduces the volume and weight of the battery, and accordingly of the implant, to a corresponding degree. A lower required valve force also reduces wear on and plastic deformation of the sealing surface, which increases the life of the valve and counteracts any change in the pumped chamber volume over time. The infusion system according to the invention also makes it possible to use the new low pressure pumping principles, discussed above, in the infusion system, since the pressure difference between the medication container and surroundings is always very small, irrespective of ambient pressure and temperature. The infusion system according to the invention completely eliminates cavitation in the pump, thereby reducing damage to the pump fluid. Moreover, deposits on the valve and other surfaces in contact with the fluid are reduced without the need to reduce the force of piston retraction, i.e. the margin relative to piston "hangup" can be kept unchanged. Further, the penetration of body fluid, air or any other gas through the refill septum is eliminated by the infusion system according to the invention throughout its service life. The above-described cause of a loss in pumped volume and the attendant cause of catheter blockage due to bulging of the valve sealing washer are eliminated by the infusion system according to the invention.

With the infusion system according to the invention, a pressure difference essentially equal to zero is assured across the outlet valve and across the refill septum, and no fluid or air can then leak in during pump operation or container refilling at any time during the service life of the system, even if the valve and/or refill septum are no longer completely leak-proof because of wear. The service life of the infusion system and its ability to keep its specifications within narrow limits throughout the service life of the system increase considerably. Additionally there is no risk of medication leakage, since the container and surroundings are at the same pressure.

In an embodiment of the system according to the invention, a part of the lateral wall of the enclosure is covered by an elastic membrane with low stiffness, which is radially expandable and contractible in order to keep the volume of the enclosed space outside the container constant when the volume of the supply container changes. The upper part of the enclosure is connected to the bottom by at least two bridges to give the enclosure the required mechanical stability. The advantage of this design is that the enclosure becomes insensitive to common forms of mechanical pressure imposed on the implanted system, such as a tight belt, pressure on the abdomen etc. In addition, any increase in the thickness of the implant, which could occur in previously described versions when the supply container is full, is also completely avoided.

According to another embodiment of the system of the invention, the enclosed space encompasses an expansion chamber connected to the chamber inside the enclosure (housing) in which the supply container is arranged. The expansion chamber is arranged to change its volume in the same way as the supply container. The expansion chamber is connected to the chamber inside the enclosure by a flexible tube. The expansion chamber can be arranged inside the peritoneum or in the abdominal wall. The advantage of arranging the expansion chamber in the peritoneum is that the tip of the catheter and expansion chamber will then be close to each other and accordingly exposed to the same pressure, irrespective of variations in external pressure and tension in the patient's abdominal musculature. This also makes the system insensitive to external mechanical pressure, since the expansion chamber then lies inside the muscle bed, and organs in the abdominal cavity are soft. Thus a local mechanical pressure would cause practically no pressure difference between the catheter tip and the expansion chamber. Leakage of fluid through the catheter would therefore be impossible, and entrances through the skin would not be needed. Moreover, the expansion chamber does not expand and contract inside body tissue, but instead does so inside a body cavity. The tube can have different lengths, and preferably the tube is comparatively long and tunneled laterally through the tissue before entering the peritoneum, since this reduces the risk of any infection in the implant pocket spreading and causing peritonitis. The advantage of placing the expansion chamber in the abdominal wall is that the implantation procedure is simpler with fewer risks of complications.

In the procedure for placing the expansion chamber in the abdominal wall, the expansion chamber is preferably provided with a port, closed with a septum. The supply container can thereby be refilled without the use of positive pressure. When a syringe containing fresh medication is mounted on a cannula arranged in the refill port and an empty syringe is arranged in the port of the expansion chamber, medication can be sucked into the supply-container by withdrawing the piston in the empty syringe connected to the expansion chamber. This reduces the risk of medication leakage during refilling.

In other embodiments of the system according to the invention, the supply container must be refilled by applying a small positive pressure to the syringe connected to the refill port. According to another advantageous embodiment of the system of the invention, the refill port of the supply container is equipped with a cannula sensor which detects correct insertion of the cannula for refilling the supply container. This eliminates the risk of medication being injected into the patient during the refilling procedure if the physician injects at the wrong site, the cannula fails to puncture the septum of the refill port, or the cannula slips out of the septum during the refilling procedure. The cannula sensor can detect whether the cannula really is in the refill port during the entire refilling operation.

DESCRIPTION OF THE PREFERRED EMBODIMENTS

Figure 1:
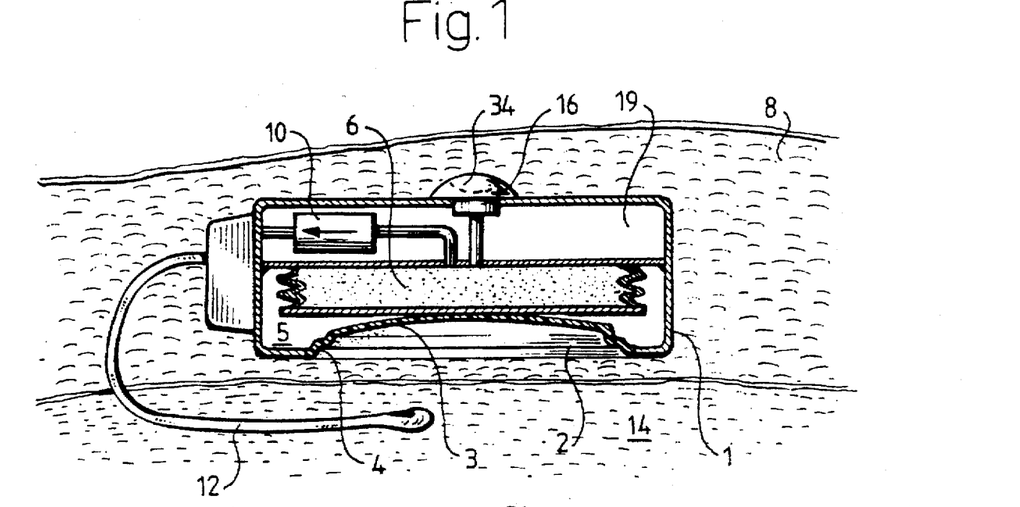
FIG. 1 is a side sectional view of a first embodiment of an infusion system constructed in accordance with the principles of the present invention showing the supply container partially emptied.
Figure 2:
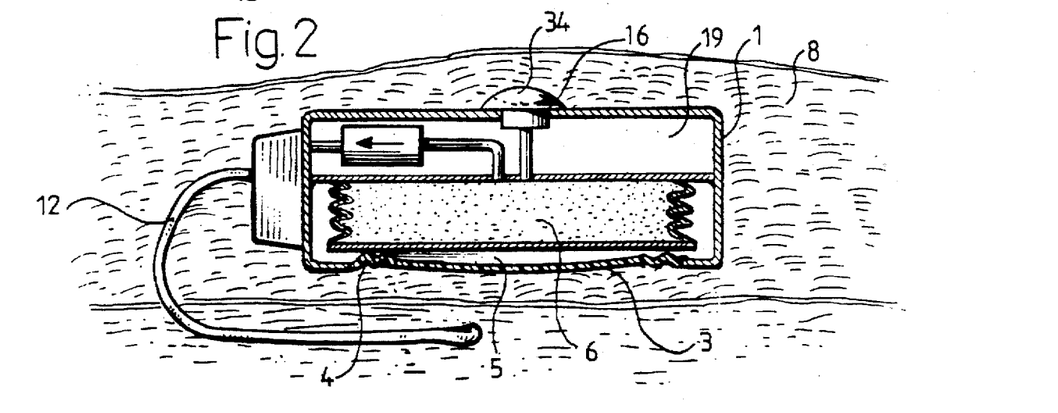
FIG. 2 shows the same sectional view as in FIG. 1, but with a filled supply container.
Figure 3:
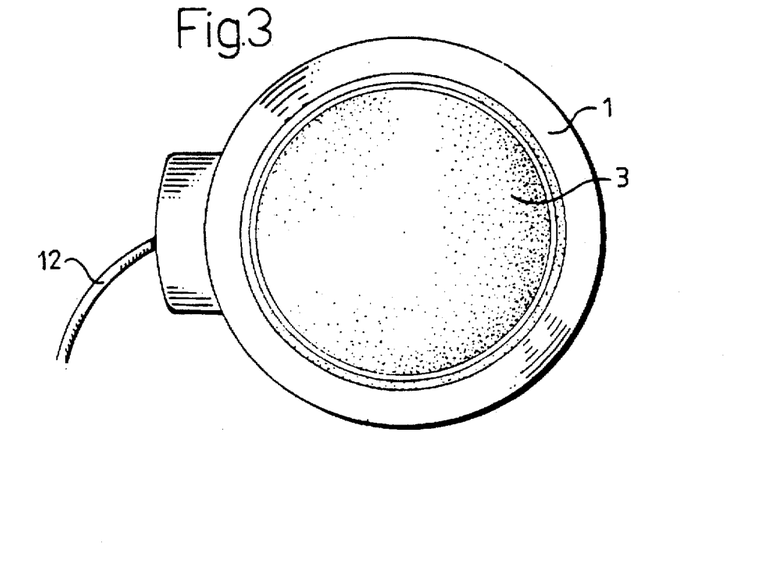
FIG. 3 is a top view of the infusion system as shown in FIGS. 1 and 2, shown in a slightly reduced size.

FIGS. 1 to 3 show a first embodiment of the infusion system according to the invention, implanted in the abdominal wall 8 of a patient. The infusion system has a supply container 6 for medication, e.g. an insulin container devised as a bellows container. The supply container 6 is completely diffusion-proof and preferably made of metal. A pump 10 is arranged to pump medication from the container 6 to the catheter 12, which opens into the patient's peritoneum 14. The supply container 6 is further connected to a refill port 16 equipped with a leak-proof rubber septum. The container 6, the pump 10, and the requisite electronics (which are known and therefore not shown) for control and communication, and the battery for powering the operation of the system are enclosed in a leak-proof enclosure (housing)1. The pump 10, the electronics and battery are situated in the hermetically sealed chamber 19 of the enclose 1. The enclosure 1 is preferably made of titanium and has an opening 2, preferably circular, in the bottom. The opening is covered by an elastic membrane 3 with low stiffness. The membrane 3 can appropriately be made of a polymer with good mechanical properties, poor water diffusion and good biocompatibility. The membrane 3 can be provided with bellows folds 4 to reduce the stiffness and the stress on the material when the membrane moves. The membrane can be a laminate of a plurality of layers with differing mechanical, physical and biological properties. One of the layers can consist of a metallic coating to reduce the diffusion of fluid and gas. Alternatively, the membrane 3 can be made of thin sheet metal with bellows folds and/or corrugation, so that sufficient elasticity is achieved.

The enclosure 1 with the membrane 3 should be diffusionproof. This provides double protection against leakage of medication into the patient's body. If a leak were to occur in the supply container 6, the enclosure 1 with the membrane 3 then prevents medication from leaking into the patient.

The space 5 inside the enclosure in which the supply container 6 is arranged can be filled with a gas at atmospheric pressure and with large molecules to reduce the diffusion of gas. The space can alternatively be filled with a liquid, e.g. water or a liquid with a high molecular weight and appropriate chemical and physical properties in order to prevent outward diffusion. The liquid can be isotonic for reducing or eliminating diffusion. One such appropriate liquid is a physiologically compatible sodium chloride (saline) solution.

In the embodiment of FIGS. 1-3, the pressure in the space 5, the supply container 6 and the abdominal cavity is essentially the same and equal to the atmospheric pressure when the bellows of the supply container 6 and the membrane 3 are properly designed.

When the supply container 6 collapses as it empties of medication, the space 5 decreases to a corresponding degree by bulging the membrane 3 inwardly such that the pressure is maintained constant. When the medication container 6 expands during refilling, the membrane also expands, so that the space 5 becomes larger, and the pressure is maintained constant.

Thus, the membrane 3 bulges inwardly when the container 6 is nearly empty, whereupon soft body tissue in the abdominal wall 8 might also bulge inwardly, possibly with a slight negative pressure, i.e. up to about 10 mbars, developing in the container 6 as a result. Since a medication container 6 in service empties very slowly, the inward bulge of the membrane 3 will fill with extracellular liquid, and no negative-pressure will therefore develop in the tissue in practice.

When the medication container 6 is refilled, the membrane 3 reverses its bulge (see FIG. 2) and a slight positive pressure, i.e. up to about 10 mbars, could develop in the supply container 6 and persist for some time, i.e. a few hours or a day. In practice, these minor pressure differences, of maximally ±10 mbars for a limited period of time, are of no importance.

When the supply container is full, a mechanical pressure on the implant could generate positive pressure in the container which in certain circumstances could be a shortcoming. A pressure force of 30N on the top of the implant in the currently used design of implanted equipments corresponds to a positive pressure in the supply container of about 60 mbars. Such a mechanical pressure for a long period of time is highly unlikely and would be painful to the patient and need not be feared in normal conditions.

After emptying of the supply container 6, the refilling of medication in the embodiment according to FIGS. 1-3 must be performed by the application of weak positive pressure to the syringe, containing fresh medication, connected to the refill port 16, i.e. pressure is cautiously applied to the syringe piston. There is a risk that medication is then injected into the patient, if the physician injects at the wrong site and the cannula has not punctured the septum of the refill port 16 or the cannula slips out of the septum. These risks can be eliminated if a cannula sensor 18 or 20 is arranged to detect whether the cannula actually is inside the refill port 16 throughout the entire refilling operation.

Figure 4:
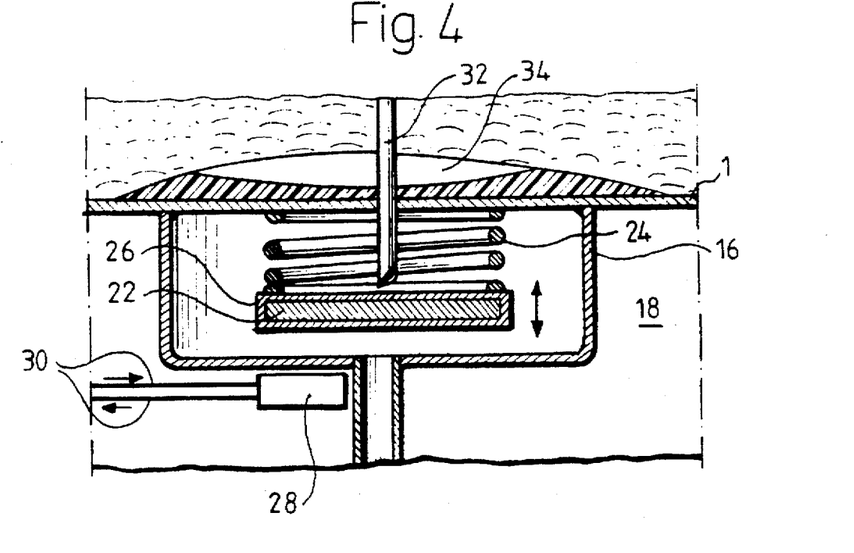
FIG. 4 is an enlarged sectional view of the refill port in the infusion system of the invention in the embodiment shown in FIGS. 1–3, with a cannula sensor.

FIG. 4 shows the cannula sensor 18, only schematically indicated in FIG. 1, in greater detail. Thus, FIG. 4 shows a cannula sensor with a disc-shaped permanent magnet 22 suspended by a spring 24 inside the refill port 16. The magnet 22 is magnetized perpendicularly to the disc plane and is hermetically sealed inside an enclosure 26 made of, e.g., pure titanium. The spring device 24 can suitably be devised as a pure titanium or titanium alloy coil spring, the spring 24 keeping the magnetic disc 22 a short distance above the bottom of the port 16.

A gauge 28, which senses when the magnet 22 is approaching, is arranged below the bottom of the port 16. The gauge 28 can be a magnetoresistive gauge in the form of a Hall-plate connected, by lines 30, to an electronic detection circuit (not shown), When the cannula 32 penetrates the septum 34, the magnetic disc 22 with its enclosure 26 serves as a stop for the cannula 32 and the combination of the disc 22, and the enclosure 26 is pressed towards the bottom of the port 16 and activates the gauge 28. Telemetry equipment can be used to ascertain that the disc 22 remains depressed throughout the whole refilling operation, thereby confirming that the cannula 32 has been in the right position the entire time.

Other types of gauges are conceivable in the cannula sensor as well, e.g. piezoelectric gauges.

Figure 5:
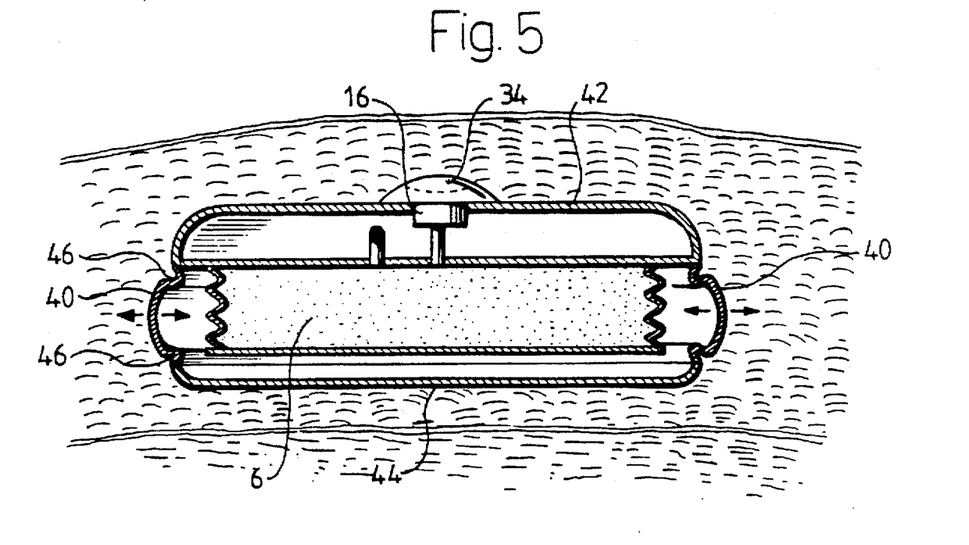
FIG. 5 is a side sectional view of a second embodiment of an infusion system constructed in accordance with the principles of the present invention.
Figure 6:
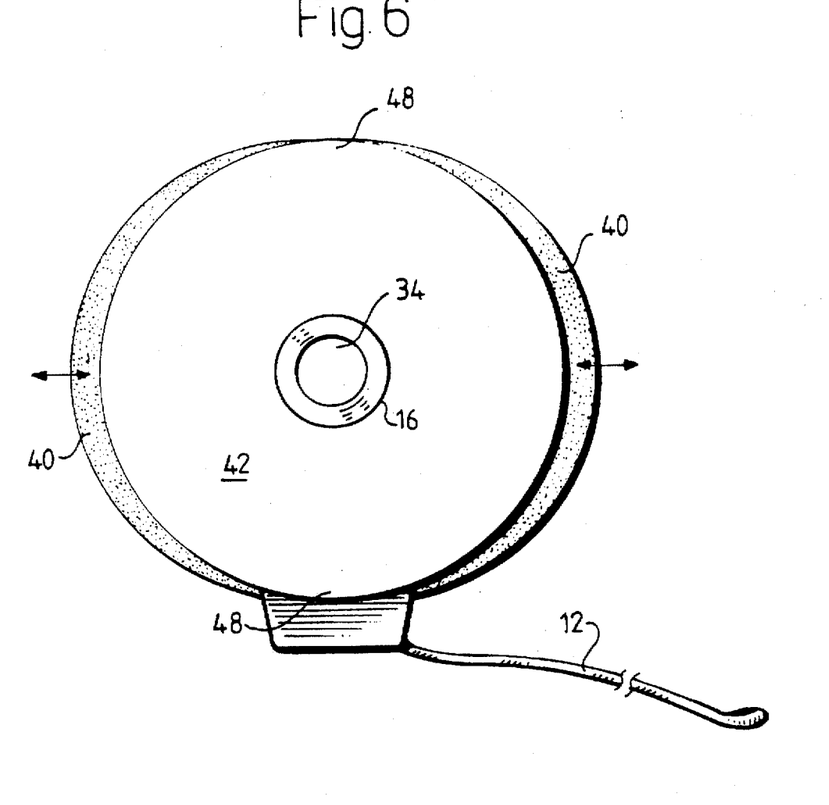
FIG. 6 is a top view of the second embodiment of the infusion system shown in FIG. 5.

FIGS. 5 and 6 respectively show cross-sections from the side and from above of a second embodiment of the infusion system according to the invention. This embodiment generally resembles the embodiment according to FIGS. 1-3 with the difference that a part of the lateral wall of the enclosure consists of an elastic membrane 40 which expands and contracts radially in order to change the volume of the space 5. The membrane 40 extends around most of the implant's periphery and is attached to the rigid upper section 42 and the bottom section 44 of the enclosure, possibly by bellows folds 46.

The upper section 42 and the bottom section 44 are suitably made of titanium and connected to each other by at least two rigid bridges 48 to give the construction the required mechanical stability.

The embodiment according to FIGS. 5 and 6 functions in the same way as the embodiment in FIGS. 1–3. The advantage of the former construction is that it is insensitive to natural mechanical pressures to which the implant is subjected, such as pressure from a tight belt and pressure on the abdomen. Moreover, the slight increase in implant thickness which possibly can occur when the supply container 6 in the embodiment shown in FIGS. 1–3 is full is avoided.

Figure 7:
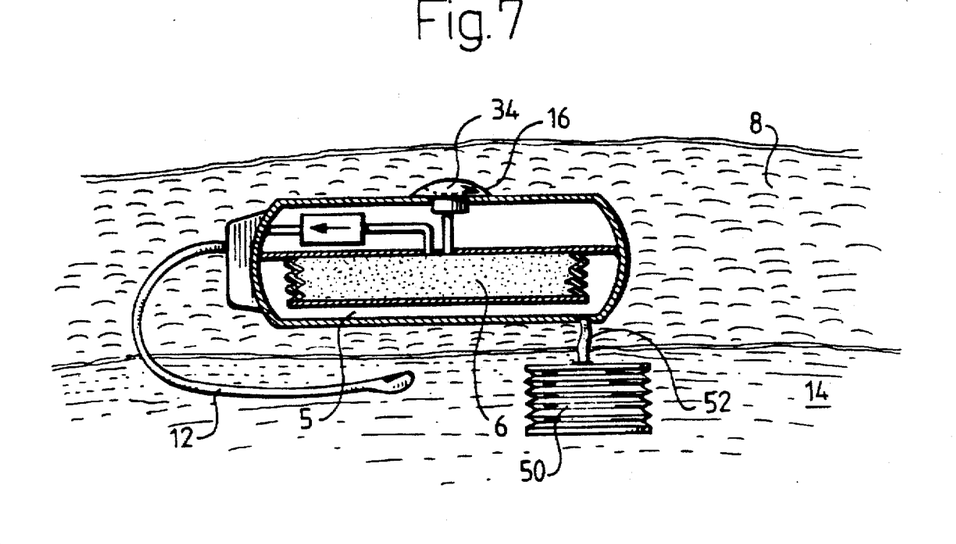
FIG. 7 is a side sectional view of a third embodiment of an infusion system constructed in accordance with the principles of the present invention.

In the embodiment according to FIG. 7, the space 5, in which the supply container 6 is arranged, is connected to an expansion chamber 50 by a flexible tube 52, essentially atmospheric pressure also prevailing in the expansion chamber. The expansion chamber 50 is expandable and contractible and is placed in the peritoneum 14.

The expansion chamber 50 can have the same volume as the medication container 6, and its resistance to expansion and contraction is low. An appropriate material for the expansion chamber 50 can be a polymer or a laminate of a plurality of polymers with appropriate mechanical, physical and biological properties, possibly with a metallization to impede diffusion. The expansion chamber 50 can alternatively be made of thin sheet metal, e.g. pure titanium or titanium alloy.

In the embodiment shown in FIG. 7, the tube 52 is relatively short, but it can be longer and tunneled laterally through the tissue before entering the peritoneum 14. The use of a long tube 52 reduces the risk of any infection in the implant pocket spreading and causing peritonitis.

The tube 52 is diffusion-proof. The tube 52 can thus be, e.g., metallized. The tube 52 can be a composite tube with a polyethylene interior and a silicone rubber exterior and can be reinforced with an embedded metal helix, by fiber reinforcement or the like to prevent tube kinking.

The inlet the abdominal cavity can be provided with a Dacron® cuff (not shown) or the like for attachment and sealing.

The expansion chamber 50 and the space 5 can be filled with air or some other gas, appropriately a gas with large molecules to reduce diffusion, or a liquid, such as water, or a liquid with a high molecular weight and appropriate physical chemical properties, such as an isotonic liquid, to prevent diffusion.

The advantage of this embodiment is that the expansion chamber 50 and the catheter tip are both inside the peritoneum 14, relatively close to each other, and are therefore subjected to the same pressures, irrespective of variations in external pressure and irrespective of tension in the patient's abdominal musculature. This embodiment of the infusion system according to the invention is also insensitive to external mechanical pressure, since the expansion chamber 50 lies inside the muscle bed, and organs in the abdominal cavity are soft. Even in instances of a local mechanical pressure, there is almost no pressure difference between the catheter tip and the expansion chamber 50. There is accordingly no leakage of fluid through the catheter 12. Other advantages are that patient skin entrances are unnecessary and expansion and contraction to achieve the required changes in volume occur in a body cavity, not in body tissue.

A weak positive pressure must be applied to the refill syringe when the supply container 6 is filled, which can have shortcomings as discussed above. These shortcomings can be eliminated, however by providing a cannula sensor of the kind described above in conjunction with FIG. 4.

Figure 8:
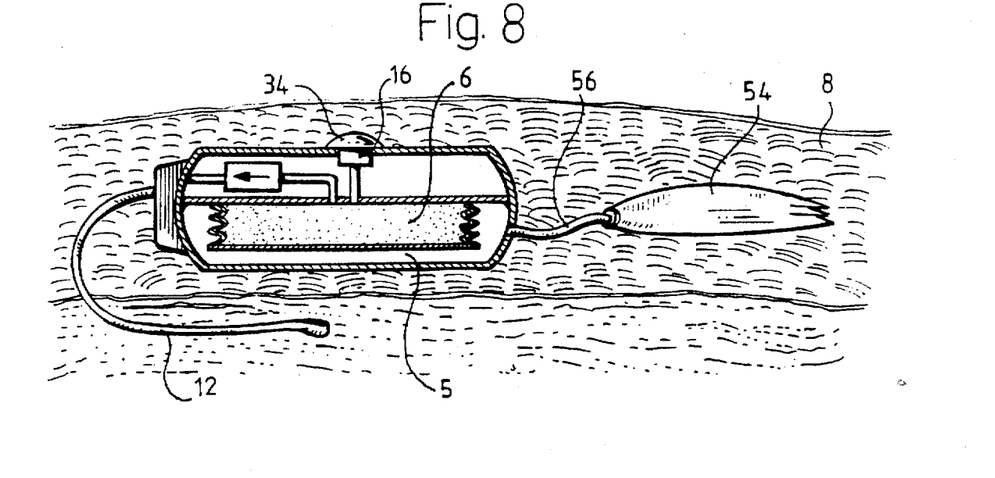
FIG. 8 is a side sectional view of a fourth embodiment of an infusion system constructed in accordance with the principles of the present invention.

FIG. 8 shows yet another embodiment of the infusion system according to the invention, with an expansion chamber 54 implanted in the abdominal wall 8 alongside the infuser. The expansion chamber 54 appropriately has a relatively large area in the plane of the abdominal wall 8 so its thickness and changes in thickness will be as small as possible. The connecting conduit 56 is easily flexible and has the same properties as the connecting conduit 52 in the embodiment according to FIG. 7. In other respects, this embodiment works in the same way as the embodiment shown in FIG. 7, i.e. when the volume of the supply container 6 changes during the emptying or filling of medication, the volume of the expansion chamber 54 changes to a corresponding degree, so that a neutral pressure is maintained in the whole closed space.

The advantage of the embodiment of FIG. 8 compared to the embodiment shown in FIG. 7 is that the implantation procedure is simpler and the risk of complications is reduced. The embodiment of FIG. 8, however, has greater sensitivity to local mechanical pressure on the patient.

Also in this embodiment, the supply container 6 is refilled with a weak positive pressure applied to the refill syringe and to minimize the risks to the patient a cannula sensor of the above-described kind can also be utilized in this case.

Figure 9:
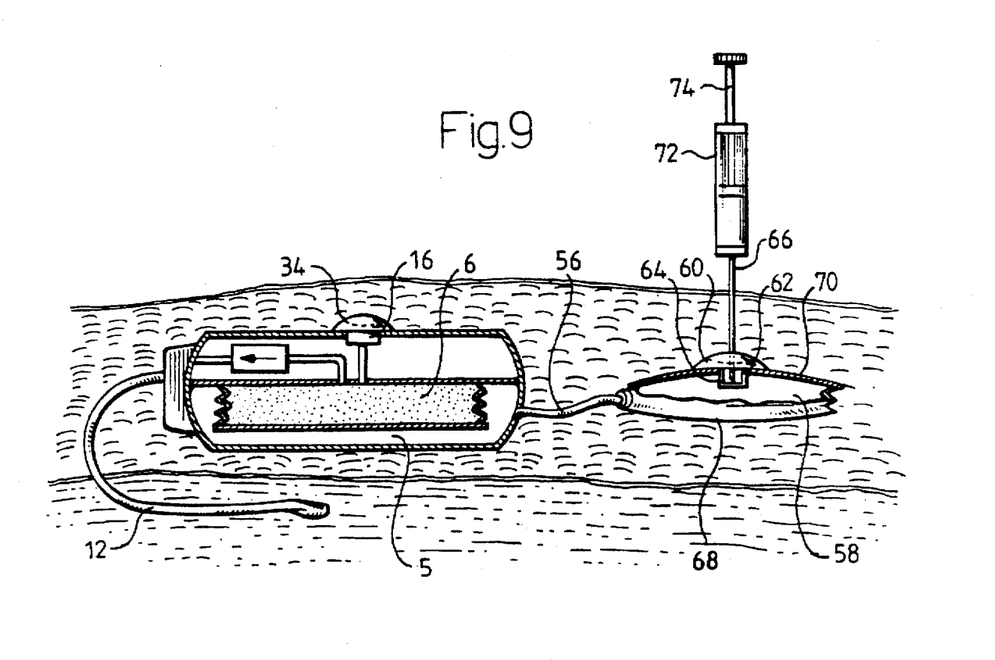
FIG. 9 is a side sectional view of a further version of the embodiment of FIG. 8, illustrating a filling procedure.

FIG. 9 shows a refinement of the embodiment in FIG. 8 in which the expansion chamber 58 is equipped with a port 60 covered by a septum 62 in the same way as the refill port 16 of the infuser itself. The port 60 is equipped with a strap 64, serving as a cannula stop, to prevent the cannula 66 from being inserted too far and damaging the opposite wall 68 of the expansion chamber 58. Moreover, the upper part of the expansion chamber 58 is provided with a shield 70 made of a harder, thicker material, such as titanium sheet or a polymer material, to prevent damage to the expansion chamber if an incorrect puncture is applied with the cannula 66.

In this embodiment, the supply container 6 can be refilled without the use of positive pressure. In refilling, any residual insulin is first removed with a syringe and cannula through the septum 34. A syringe with fresh insulin is then attached to the same cannula. An empty syringe 72 is inserted through the septum 62 of the expansion chamber 58, and insulin is drawn into the container 6 when the piston 74 of the syringe 72 is retracted. In this manner, the risk of medication leakage is completely eliminated, and no cannula sensor is needed in the refill port 16.

Once the correct amount of medication has been sucked into the supply container 6, the cannula in the refill septum 34 is removed, and the contents of expansion chamber 58 (air, gas, liquid) sucked out by the syringe 72 are transferred to the expansion chamber 58 in order to restore neutral pressure before the cannula 66 is withdrawn from the septum 62.

In other respects, the embodiment according to FIG. 9 works in the same way as the embodiment according to FIG. 8.

Although modifications and changes may be suggested by those skilled in the art, it is the intention of the inventor to embody within the patent warranted hereon all changes and modifications as reasonably and properly come within the scope of his contribution to the art.

I claim as my invention:

1. An implantable infusion system comprising:

a housing adapted for implantation in a patient;

a neutral pressure medication supply container disposed in aid housing for containing liquid medication to be administered to said patient, at least a portion of said medication container being flexible so that said container has a volume which changes dependent on an amount of medication contained in aid medication container;

a catheter connected to an exterior of said housing and adapted for implantation in the body of said patient with a tip of said catheter disposed at a medication delivery site;

pumping means, disposed in aid housing and connecting an interior of said medication container to said catheter for pumping medication from said medication container to said catheter; and means for defining a closed space in which said medication container is disposed, said means for defining a closed space having a volume at least partially contained in said housing, and having a flexible wall portion means exposed to an exterior of said housing, for causing the volume of said closed space to change by a corresponding amount when the volume of said medication container changes for maintaining a pressure acting on said supply container substantially constant.

2. An implantable fusion system as claimed in claim 1 wherein said flexible wall portion means comprises a portion of said housing which is flexible and which has an original shape, said flexible portion of said housing bulging inwardly into said housing when the volume of said medication container decreases and returning toward said original shape when the volume of said medication container increases for maintaining the volume of said closed space outside of said medication container substantially constant.

3. An implantable infusion system as claimed in claim 2 wherein said housing has an opening and wherein said flexible portion of said housing comprises an elastic membrane having low stiffness covering said opening.

4. An implantable infusion system as claimed in claim 3 wherein said housing has a bottom and wherein said opening is disposed in said bottom of said housing.

5. An implantable infusion system as claimed in claim 3 wherein said housing has a lateral wall and wherein said opening is disposed in said lateral wall.

6. An implantable infusion system as claimed in claim 5 wherein said housing has an upper part and a lower part with said opening disposed there between, and said housing further having at least two rigid ridges connecting said upper part and said lower part.

7. An implantable infusion system as claimed in claim 3 wherein said means for defining said closed space further comprises bellows folds attaching said membrane to said housing.

8. An implantable infusion-system as claimed in claim 3 wherein said membrane consists of a polymer.

9. An implantable infusion system as claimed in claim 3 wherein said membrane consists of thin sheet metal with bellows folds.

10. An implantable infusion system as claimed in claim 3 wherein said membrane consists of thin sheet metal with corrugations.

11. An implantable infusion system as claimed in claim 3 wherein said membrane consists of a multi-layer laminate.

12. An implantable infusion system as claimed in claim 11 wherein one layer of said multi-layer laminate consists of metal.

13. An implantable infusion system as claimed in claim 1 wherein said means for defining said closed space includes an expansion chamber disposed outside of said housing and connected by a fluid communication path with a volume inside said housing in which said medication container is disposed.

14. An implantable infusion system as claimed in claim 13 wherein said expansion chamber has a volume equal to the volume of said medication container.

15. An implantable infusion system as claimed in claim 13 wherein said expansion chamber is comprised of a polymer.

16. An implantable infusion system as claimed in claim 13 wherein said expansion chamber comprises a multi-layer laminate.

17. An implantable infusion system as claimed in claim 13 wherein said expansion chamber comprises a multi-layer laminate including a plurality of polymer layers.

18. An implantable infusion system as claimed in claim 17 wherein said laminate includes a metal layer.

19. An implantable infusion system as claimed in claim 13 wherein said expansion chamber comprises sheet metal.

20. An implantable infusion system as claimed in claim 19 wherein said expansion chamber comprises sheet metal selected from the group consisting of pure titanium and titanium alloys.

21. An implantable infusion system as claimed in claim 13 wherein said expansion chamber is adapted for implantation in the abdominal wall of said patient, and wherein said expansion chamber has a large area in a first plane parallel to said abdominal wall and a small thickness in a second plane perpendicular to said first plane.

22. An implantable infusion system as claimed in claim 13 wherein said means for defining said closed space further includes a flexible tube connecting said expansion chamber and said housing for placing an interior of said expansion chamber include communication with an interior of said housing.

23. An implantable infusion system as claimed in claim 22 wherein said flexible tube comprises diffusion-proof material.

24. An implantable infusion system as claimed in claim 22 wherein said flexible tube comprises a composite tube having a polyethylene interior and a silicone rubber exterior.

25. An implantable infusion system as claimed in claim 22 wherein said flexible tube includes a reinforcement selected from the group consisting of a metal helix and reinforcement fibers.

26. An implantable infusion system as claimed in claim 22 wherein said flexible tube has a metal exterior coating.

27. An implantable infusion system as claimed in claim 13 wherein said expansion chamber comprises a port closed by a septum.

28. An implantable infusion system as claimed in claim 27 wherein said expansion chamber has a wall in which said port is disposed, said wall comprising a shield consisting of hard or thick material.

29. An implantable infusion system as claimed in claim 27 wherein said expansion chamber further comprises a cannula stop disposed inside said port in said expansion chamber.

30. An implantable infusion system as claimed in claim 1 further comprising a molecular gas filling said closed space, composed of molecules too large to diffuse out of said closed space.

31. An implantable infusion system as claimed in claim 1 further comprising a molecular liquid filling said closed space, composed of molecules with a molecular weight too high to diffuse out of said closed space.

32. An implantable infusion system as claimed in claim 31 wherein said high molecular weight liquid comprises a physiologically compatible sodium chloride solution.

33. An implantable infusion system as claimed in claim 1 wherein said medication container includes a refill port and cannula sensor means for depicting direct insertion of a cannula into said refill port for refilling said medication container.

34. An implantable infusion system as claimed in claim 33 wherein said cannula sensor means comprises:

a disc-shaped permanent magnet;

means for suspending said disc-shaped permanent magnet relative to said port with a spring bias urging said disc-shaped permanent magnet toward said port; and gauge means, disposed at a bottom of said port, for sensing when said magnet is moved close to said bottom of said port by a cannula inserted into said port.

35. An implantable infusion system as claimed in claim 34 wherein said gauge means comprises a magneto-restrictive gauge connected to an electronic detection circuit.

* * * * *